United States Patent [19]

Bernstein

[11] 4,061,138
[45] Dec. 6, 1977

[54] TOE PROTECTOR AND FOOT SUPPORT FOR AN ORTHOPEDIC CAST

[76] Inventor: Jacob Bernstein, 4840 Morse, Lincolnwood, Ill. 60646

[21] Appl. No.: 713,862

[22] Filed: Aug. 12, 1976

[51] Int. Cl.$^2$ ............................................ A61F 13/00
[52] U.S. Cl. ..................................... 128/82; 128/83.5
[58] Field of Search .......................... 128/83.5, 83, 82; 36/11.5, 2.5 R, 7.5

[56] References Cited

U.S. PATENT DOCUMENTS

| 3,263,679 | 8/1966 | Hass | 128/83.5 |
| 3,773,041 | 11/1973 | Bogar, Jr. et al. | 128/83.5 |
| 3,916,538 | 11/1975 | Loseff | 36/11.5 |

Primary Examiner—John D. Yasko
Attorney, Agent, or Firm—Neuman, Williams, Anderson & Olson

[57] ABSTRACT

A toe protector and foot support for an orthopedic cast is provided incorporating a flat elongated tongue for supporting the foot and for facilitating the laying-up of a cast, with a forward portion having an arcuate rim affixed rigidly to the tongue, which rim encircles and protects the toes by extending to the forward part of the foot. A simplified protector and support is provided for interchangeable use with either right or left feet.

7 Claims, 4 Drawing Figures

U.S. Patent      Dec. 6, 1977      4,061,138
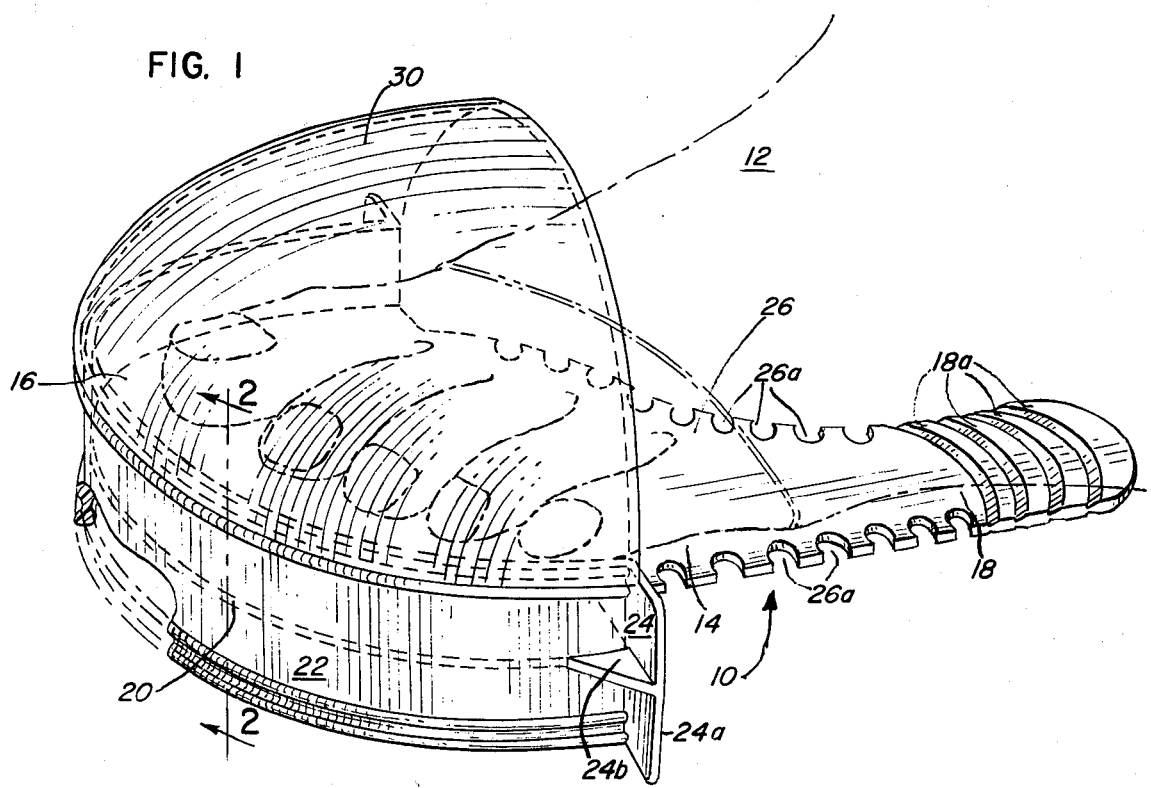
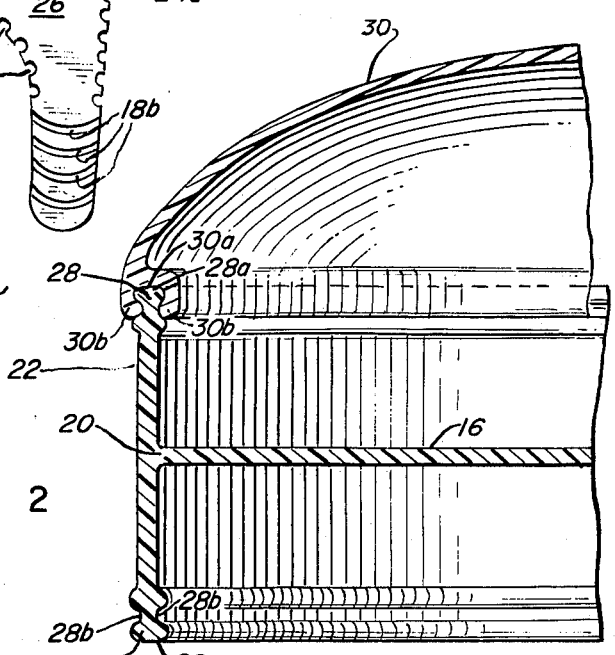
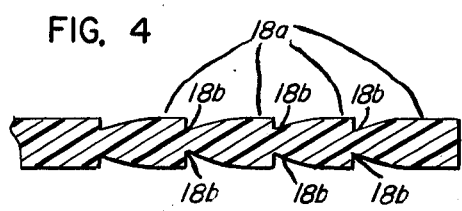

TOE PROTECTOR AND FOOT SUPPORT FOR AN ORTHOPEDIC CAST

BACKGROUND OF THE INVENTION

The present invention relates generally to plaster casts for the foot and leg, and is more specifically directed to a toe protector and foot support for use in laying-up the cast and protecting the toes which are generally not covered by the cast and extend forward therefrom. An enclosure is thus provided for the normally exposed toe area of a foot in a cast.

It is a primary object of the invention to provide a simple and effective one-piece foot support and toe protective apparatus for use in conjunction with the manufacture of a cast and the subsequent use thereof.

Another significant object of the instant invention is to provide a toe protector and foot support which may be used in making a cast for either the left or the right foot but is adapted to provide proper support and protection when used either way.

A further object of the invention is to provide a toe protector and foot support for a cast which has provision for retaining a removable toe covering.

A still further object of the invention is to provide a toe protector and foot support for a cast which can be firmly and easily anchored within the cast to give adequate support and integrity to the cast.

Yet another object of the invention is to provide a toe protector and foot support for a cast which is quickly modified to properly accomodate the length of the foot to be cast.

SUMMARY OF THE INVENTION

The improvement of a one-piece toe protector and foot support apparatus of the present invention includes an elongated tongue having notches along the rear side edges thereof for anchoring the apparatus into a foot cast and it also includes an arcuate rim connected to the forward portion for protecting the toes and providing a toe enclosure. The rim extends above and below the forward portion of the tongue and is shaped to the contour of the front of a human foot whereby the apparatus may be used on either the right or left foot by merely turning the unit over and facing upwardly the toe receiving portion of the rim which is the appropriate shape for the foot to be cast. At the rearward end of the tongue are segments defined by a series of generally transverse scores. Segments at the end of the tongue may be snapped off at a given score to custom fit the length thereof. Along the top and bottom of the rim is a beaded edge which is adapted to hold a complementary groove on a toe protecting cover shaped to extend across the rim.

The particular apparatus for toe protection and foot support is designed to accomplish the objects and advantages set forth and those which will subsequently appear in the details of construction and operation as is more fully described and claimed herein reference being had to the accompanying drawings forming a part thereof.

BRIEF DESCRIPTION OF THE DRAWINGS

FIG. 1 is a perspective view of the one-piece toe protector and foot support apparatus for a cast with a stockinged foot shown in phantom;

FIG. 2 is a cross-sectional view taken along line 2—2 in FIG. 1;

FIG. 3 is a reduced top elevational view of the toe protector and foot support shown in positions for use on either a left or right foot; and FIG. 4 is an enlarged fragmentary sectional detail illustration taken along line 4—4 of FIG.3.

DETAILED DESCRIPTION OF THE DRAWINGS

Referring more specifically to the drawings, reference numeral 10 is used to generally designate the one-piece toe protector and foot support apparatus comprising the instant invention. The foot and associated protective stocking are designated 12; and are shown in the position of use with the plaster cast material omitted. For overall clarity the plaster cast material, which is a plaster impregnated fabric commonly used to lay up casts and well-known to those skilled in the art, has been omitted from all the figures.

The apparatus 10 includes a flat elongated tongue 14 having a forward portion 16 and a rearwardly extending cast supporting end section 18. The forward portion 16 is shaped to fit beneath the toes and ball of a human foot and the supporting end section 18 is shaped to fit beneath the foot alongside the arch of the foot. The overall shape of the tongue 14 in plan view is asymmetric such that in one position it is contoured to match the bottom of a left foot and when turned over would match the shape of the right foot, see FIG. 3. Affixed to the leading edge 20 of the forward portion 16 is a rim 22 which extends above and below the forward portion 16. Rim 22 is generally perpendicular to the forward portion 16 and follows the contour of the leading edge 20 as best shown in FIGS. 1 and 3. The rim 22 terminates at the rearmost part of forward portion 16 with a pair of flanges 24 which extend outwardly from rim 22 forming a perpendicular wall facing rearwardly and generally towards the end section 18 of tongue 14. Each flange 24 provides an abutting surface 24a against which the leading edge of the plaster cast may rest. Opposite surface 24a is a supporting gusset 24b which extends from flange 24 to rim 22, in order to secure the relationship between the flange 24 and the rim 22.

The tongue 14 includes a mid section 26 at the junction of the forward portion 16 and the end section 18. Mid section 26 is designed to rest under the human foot between the ball and the bottom of the foot alongside the arch. Thus, mid section 26 is a transionally shaped part of tongue 14 as best shown in FIG. 3. Along the side edges of mid section 26 are series of notches 26a. Each such notch 26a extends through the flat elongated tongue 14 forming a generally serrated edge on each side of mid section 26. The notches are provided to present anchoring surfaces for the plaster casting material used in the process of laying up a cast.

The rear end section 18 of tongue 14 has a series of segments 18a defined by transverse scores 18b, see FIGS. 1, 3 and 4. Each segment 18a is separated by a pair of opposite transverse scores 18b, such that a conveniently presented breaking line is suggested; whereby the rearward extension of tongue 14 may be shortened to custom-fit end section 18 to a shorter foot.

Rim 22 is shown in cross section in FIG. 2. At the top and bottom edges of rim 22 are beads 28 having an enlarged top portion 28a above a pair of back-to-back recesses 28b. The beads 28 form a reinforced surface for receiving a toe cover 30, see FIG. 2. Cover 30 is generally dome-shaped to provide sufficient internal volume to comfortably contain the toes and has a downwardly depending groove 30a designed to conjugate with either bead 28. At the opening of groove 30a are inwardly facing ridges 30b which are designed to interengage in a snap fitting manner with recesses 28b. The general outline in plan of cover 30 is identical to the shape of rim 22, as shown in FIG. 3. Therefore, a left and a right cover 30 must each be provided to mate with the asymmetrically shaped rim 22.

In manufacturing or laying-up a cast, the foot is placed in a protective stocking and the plaster casting material is wrapped transversely about the mid portion of the foot covered by the stocking. After one or two layers of plaster casting material have been applied the foot is placed in position on tongue 14 with the toes protectively surrounded by the rim 22. Depending upon whether a left or right foot is being cast, the appropriate position of the one-piece apparatus 10 is selected, see FIG. 3. Similarly, the rear end section 18 can be shortened at breaking lines 18b to a custom length for the given application. The warping of the cast material continues after the inclusion of the apparatus 10 and with each successive wrap the plaster cast material engages the notches 26a on mid section 26 to firmly anchor same within the wrapped layers of the plaster casting material. Successive layers of plaster casting material are added to give adequate body to the cast, and the cast is extended to the surfaces 24a of flanges 24 which form a convenient load bearing place for receiving any axial loading which during the subsequent use thereof may be caused by bumping the rim 22 of apparatus 10. As described, cover 30 is shaped to fit above the toes and provides an easily removed protective covering by means of the interengagement of groove 30 and bead 28, such that cover 30 may be removed and replaced by the patient without need of a doctor's skill or tools.

While the one-piece apparatus 10 is preferably formed of a molded polymeric material such as polystyrene, and the cover 30 is fashioned from a resilient material, such as polyethylene and is sized for the average foot, the foregoing detailed description and drawings are considered as illustrative of the preferred embodiment, the principles and use of the invention. For example, the rim 22 need not extend both above and below the tongue 14 and the contour of the lead edge 20 may be changed to a symmetrical shape. Since numerous other modifications in the materials of construction, the particular shape and contour and the detailed features of construction will readily occur to those skilled in the art, it is not desired to limit the invention to the embodiment and operation shown and described, and accordingly all suitable equivalents which may be resorted to fall within the scope of the invention.

I claim:

1. A one-piece toe protector and foot support apparatus for incorporation in a plaster cast comprising an elongated flat tongue having a forward portion and a rear end section, a leading edge on said forward portion having the asymmetric shape of the outline of a human foot; a rim affixed to said leading edge and perpendicularly extending above and below said edge forming toe protecting enclosures for either the right or left foot depending upon which said enclosure is used.

2. The apparatus of claim 1 wherein said enclosure includes a cover; and said rim includes beaded edges along the top and bottom thereof, said cover being shaped to conjugate with at least one of said edges and having a complementary groove for mating interengagement with said edge.

3. The apparatus of claim 1 wherein said tongue includes a mid section between said forward portion and said rear end section, said mid section having serrations along the side edges thereof.

4. The apparatus of claim 1 wherein said rear end section includes a plurality of segments defined by a series of generally transverse scores in opposed relationship across the top and bottom surfaces of said rear end section.

5. The apparatus of claim 1 wherein the rearmost extending parts of said rim terminate in outwardly extending flanges which presents a rearwardly facing abutting surface and said flange extending above and below said tongue.

6. The apparatus of claim 1 wherein said tongue and said rim are a molded unit formed of a polymeric substance.

7. A one-piece toe protector and foot support apparatus for incorporation into a plaster cast comprising an elongated flat tongue for lying in a horizontal plane beneath a human foot, said tongue having the general shape of a foot including forward or toe supporting means, a middle or ball supporting means, and back or arch supporting means all for lying beneath a human foot; a rim extending upwardly from said toe supporting means at the leading edge thereof and extending rearward along said edge to said ball supporting means where said rim juts outwardly from said tongue forming backwardly facing walls, said rim extending to a height adequate to cover the toes.

* * * * *